(12) United States Patent
Lee et al.

(10) Patent No.: US 6,743,436 B1
(45) Date of Patent: Jun. 1, 2004

(54) ANESTHETIC COMPOSITION FOR INTRAVENOUS INJECTION COMPRISING PROPOFOL

(75) Inventors: Hyuk-Koo Lee, Cheonan-shi (KR); Ji-Young Jin, Jeonju-shi (KR); Hoon Cho, Cheonan-shi (KR)

(73) Assignee: Kuhnil Pharm. Co., Ltd., Cheonan-shi (KR)

( * ) Notice: Subject to any disclaimer, the term of this patent is extended or adjusted under 35 U.S.C. 154(b) by 130 days.

(21) Appl. No.: 10/018,663

(22) PCT Filed: Jun. 20, 2000

(86) PCT No.: PCT/KR00/00649

§ 371 (c)(1),
(2), (4) Date: Dec. 21, 2001

(87) PCT Pub. No.: WO00/78301

PCT Pub. Date: Dec. 28, 2000

(30) Foreign Application Priority Data

Jun. 21, 1999 (KR) ......................................... 1999/23336

(51) Int. Cl.[7] .............................. A61F 2/02; A61K 47/30
(52) U.S. Cl. ..................................... 424/423; 514/772.3
(58) Field of Search ........................ 424/423; 514/772.3

(56) References Cited

U.S. PATENT DOCUMENTS 5,714,520 A * 2/1998 Jones et al. .................. 514/731
2002/0120015 A1 * 8/2002 Dennis et al. ........... 514/772.3

* cited by examiner

*Primary Examiner*—Carlos A. Azpuru
(74) *Attorney, Agent, or Firm*—Birch, Stewart, Kolasch & Birch, LLP

(57) ABSTRACT

An anesthetic composition for intravenous injection, comprising propofol (2,6-diisopropylphenol) and Poloxamer POLOXAMER (Polyoxyethylene-polyoxypropylene copolymer) as surfactant is disclosed. The composition optionally can contain at least one co-surfactant selected from the group consisting of SOLUTOL HS 15 (Macrogol-15 Hydroxystearate), egg lecithin, LABRASOL (Polyoxy capryllic glyceride), polyoxy 10-oleyl-ether, TWEEN (polyoxyethylene sorbitan fatty acid esters), ethanol and polyethylene glycol. Because the composition is usually prepared in the form of an oil-in-water microemulsion having a particle size of 100 nm and below, it has superior technical effects in that it is thermodynamically stable and can be aseptically filtered to prevent microorganism contamination. Moreover, the composition is readily prepared so that side effects such as embolism, hyperlipidemia, etc. can be minimized.

7 Claims, No Drawings

ANESTHETIC COMPOSITION FOR INTRAVENOUS INJECTION COMPRISING PROPOFOL

This application is the national phase under 35 U.S.C. §371 of PCT International Application No. PCT/KR00/00649 which has an International filing date of Jun. 20, 2000, which designated the United States of America and was published in English.

TECHNICAL FIELD

The present invention relates to an anesthetic composition for intravenous injection comprising 2,6-diisopropylphenol (hereinafter, referred to as "propofol"). More specifically, the present invention relates to an anesthetic composition for intravenous injection, characterized in that it contains propofol and a poloxamer as the surfactant.

BACKGROUND ART

Propofol is highly lipid-soluble and has a characteristic property that it can readily permeate biomembranes such as blood brain barrier (BBB). Therefore, it has been used as a useful anesthetic agent.

In general, anesthetic agents are eliminated through their metabolism and excretion in living body. When an anesthetic agent having a long half-life is repeatedly administered in a large amount, it may be greatly accumulated into storage tissues such as skeletal muscles, adipose tissues, etc., so that the recovery may be delayed. Thus, if such anesthetic agent is administered for a long period, since it may be diffused from storage tissues into the blood to increase its plasma concentration, the recovery rate of patients may be delayed and the psychomotor function may also be damaged over long period.

Contrary to this, an alkylphenol derivative, propofol, has a short half-life and thus, has some clinical characteristic features that it can be rapidly migrated into the brain to show a rapid onset of anesthetic effect and further, rapidly re-distributed into other tissues and then metabolized so that the patients can be rapidly recovered from the anesthetic state. In addition, propofol may cause less side effects such as headache, nausea, vomiting, etc., than other anesthetic agents in patients and its accumulation into human body can be minimized in spite of its administration for a long period. Therefore, it has been known that propofol is the most ideal anesthetic agent for intravenous injection.

Further, while many anesthetic agents commonly used in the clinical field are in a gaseous state, propofol is useful for intravenous injection and therefore, can be very effectively used as a local analgesic adjuvant due to its hypnotic and sedative activities, an anesthetic agent for patients for whom pulmonary respiration should be cared, an anesthetic agent used under conscious state, etc., or for patients under medical treatment in intensive care unit (ICU) or patients in serious state, etc.

In spite of such clinical advantages of propofol, the development of its injectable formulations is very difficult since propofol exists in the non-ionized state (pKa=10.4) in blood and has physico-chemical properties including a unique high lipid solubility (octanol water partition coefficient 4.33).

Thus, since water may substantially be an essential solvent in preparing all pharmaceutical formulations including anesthetic agents, it is very difficult to formulate lipid-soluble drugs such as propofol into pharmaceutical preparations using water as the solvent. In order to solve such problem, lipid-soluble drugs which are generally poorly soluble in water have been developed into such forms as emulsions, microemulsions, micelles, etc., using a surfactant. However, it also possesses a limitation.

In the prior art, Zeneca Inc. has prepared and sold the formulation wherein 1% propofol is dissolved in 16% CREMAPHOR EL (Polyoxyl 35 castor oil) as a non-ionic surfactant. However, this formulation causes some side effects such as anaphylactoid reaction as an allergic reaction in some patients, which is believed to be caused by CREMAPHOR EL (Polyoxyl 35 castor oil) contained therein in an excessive amount. Therefore, in order to overcome such side effects caused by the surfactant Zeneca Inc. has developed the injectable formulation (trade name: Diprivan) in the form of a novel fat emulsion, wherein 1% propofol is dissolved in 10% soybean oil and then stabilized with 1.25% egg phosphatide.

However, it has been indicated that the emulsions for intravenous injection containing lipid materials have many side effects and problems, which can be generally and roughly summarized as the following five issues:

First, the emulsion is thermodynamically unstable and therefore, is fused in the course of time to make the formulation unstable.

Second, there is a possibility of causing embolism due to particles in size of 1 µm or more which may possibly be present in heterogeneous emulsions.

Third, the active ingredient and lipid components may cause a pain when the formulation is injected.

Fourth, since the lipid component may serve as a cause of the acceleration of microorganism growth in the absence of any preservative, strict aseptic techniques must be maintained when handling these formulation.

Finally, the administration of lipid components as the main ingredient may result in hyperlipidemia.

Thus, in the field of anesthesiology, the development of novel formulation which can solve the above-mentioned problems has been on the rise as the forefront subject. In thᴏÅis regard, Zeneca Inc. has developed the formulation comprising a novel composition having an antiseptic activity by addition of a preservative (EDTA) in order to inhibit the microorganism growth due to lipid components amongst the above-mentioned problems (U.S. Pat. No. 5,714,520). However, this formulation still has the unsolved problems including physical unstability, pain at injection site, embolism, hyperlipidemia, Further, in order to improve such problems, the formulations have recently been studied using inclusion complexation of propofol with biodegradable surfactants or cyclodextrin (Giuseppe Trapani et al., *J. Pharm. Sci.*, 1998, 87, 514–518), the concept of prodrugs (Sagara Y., *J. Neurochem.*, 1999, 73, 2524–2530), etc. In addition, the study to reduce the pain during injection by administration in combination with such neuroblocking agents as lidocain has been actively and extensively practiced from all parts of the world (Parmar A. K., *Anaesthesia*, 1998, 53, 79–83). However, such study has not been verified for their effect as yet and thus, not been actually completed. Therefore, the need an anesthetic composition for intravenous injection, which is capable of providing the efficient formulation and minimized side effects, has been very gradually increased.

Thus, the technical subject of the present invention is to provide a useful anesthetic composition for intravenous injection which can be efficiently converted into the desired formulation and further, can minimize the side effects, with overcoming the above-mentioned problems involved in the prior art.

DISCLOSURE OF THE INVENTION

The technical subject of the present invention is to provide a useful anesthetic composition for intravenous injection which can be efficiently converted into the desired formulation and further, can minimize the side effects, with overcoming the above-mentioned problems involved in the prior art.

In order to achieve said technical subject, the present invention provides an anesthetic composition for intravenous injection, which comprises propofol and a poloxamer as the surfactant.

According to the present invention, it is preferred that propofol is contained in an amount of 1 to 2% by weight of the total composition.

Further, the composition of the present invention may additionally contain at least one co-surfactant selected from the group consisting of SOLUTOL HS 15 (Macrogol-15 Hydroxystearate), egg lecithin, LABRASOL (Polyoxy capryllic glyceride), polyoxy 10 oleyl ether, TWEEN (polyoxyethylene sorbitan fatty acid esters), ethanol and polyethylene glycol, in addition to a Poloxamer POLOXAMER (Polyoxyethylene-polyoxypropylene copolymer) as the surfactant.

In the present invention, it is particularly preferred to use POLOXAMER 407 (Polyoxyethylene-polyoxypropylene copolymer) as the POLOXAMER (Polyoxyethylene-polyoxypropylene copolymer). It is desirable to have POLOXAMER 407 (Polyoxyethylene-polyoxypropylene copolymer) in an amount of 0.1 to 5% by weight of the total composition.

In addition, the composition of the present invention is preferably present in the form of an oil-in-water microemulsion having a particle size of 100 nm and below.

In the composition of the present invention, it is preferred that the content of propofol amounts to 1 to 2% by weight of the total composition and the content of POLOXAMER (Polyoxyethylene-polyoxypropylene copolymer) amounts to 0.1 to 10% by weight of the total composition. The POLOXAMER (Polyoxyethylene-polyoxypropylene copolymer) which can be preferably used in the present invention include POLOXAMER 407 (Polyoxyethylene-polyoxypropylene copolymer) and POLOXAMER 188 (Polyoxyethylene-polyoxypropylene copolymer), with POLOXAMER 407 (Polyoxyethylene-polyoxypropylene copolymer) being particularly preferable in providing the effect of the present invention. In case of POLOXAMER 407 (Polyoxyethylene-polyoxypropylene copolymer), it is preferably contained in an amount of 0.1 to 5%, by weight of the total composition.

Further, the composition of the present invention can additionally contain an agent for pH adjustment and an agent for isotonicity. The agent for pH adjustment is preferably sodium hydroxide and the agent for isotonicity is particularly preferable to use glycerol.

BEST MODE FOR CARRYING OUT THE INVENTION

Hereinafter, the present invention will be more specifically explained.

The composition of the present invention is characterized in that it contains propofol and a poloxamer as the surfactant.

The poloxamers are a block copolymer composed of hydrophilic polyoxyethylene and hydrophobic polyoxypropylene, which allows that in the aqueous solution the lipid-soluble portion formed from polyoxypropylene can include the drug therein and the hydrophilic polyoxyethylene portion is placed on the outside of the core so that it can be hydrated with water. All of poloxamers have a substantially similar composition to each other and are classified into many varieties depending on the ratio of polyoxyethylene/polyoxypropylene content. The poloxamers are a very stable material to exist in a stable state in an aqueous solution containing acids, alkalis and even the metals. In addition, they have been known as being a non-toxic and non-irritant material which is not metabolized in a living body. Poloxamers are described in USP XXIII and have been once used as a stable excipient by U.S. Food and Drug Administration (FDA). Further, they have been known as having less side effects than others when they are intravenously injected.

The present invention provides an anesthetic composition for intravenous injection which contains propofol and poloxamer alone or in combination with other co-surfactant.

In the composition of the present invention, it is preferred that the content of propofol amounts to 1 to 2% by weight of the total composition and the content of poloxamer amounts to 0.1 to 10% by weight of the total composition. The poloxamer which can be preferably used in the present invention include poloxamer 407 and poloxamer 188, with poloxamer 407 being particularly preferable in providing the effect of the present invention. In case of poloxamer 407, it is preferably contained in an amount of 0.1 to 5% by weight of the total composition.

Since poloxamers used in the present invention can allow the microemulsification of the composition even by using a smaller amount than prior surfactants., the toxicity of anesthetic composition containing propofol as the active ingredient can be significantly reduced.

The composition of the present invention can additionally contain at least one co-surfactant selected from the group consisting of SOLUTOL HS 15 (Macrogol-15 Hydroxystearate), egg lecithin, LABRASOL (Polyoxy capryllic glyceride), polyoxy 10 oleyl ether, TWEEN (polyoxyethylene sorbitan fatty acid esters), ethanol and polyethylene glycol, with SOLUTOL HS 15 (Macrogol-15 Hydroxystearate) and egg lecithin being particularly preferable. When SOLUTOL HS 15 (Macrogol-15 Hydroxystearate) is added in an amount of 0.1 to 10% by weight of the total composition or egg lecithin is added in an amount of 0.1 to 5% by weight of the total composition, they can show the most excellent effect.

According to the preferable embodiment of the present invention, the composition of the present invention is in the form of an oil-in-water microemulsion having a particle size of 100 nm and below.

The microemulsions have the particle size of 100 nm and below, are thermodynamically stable and do not cause any phase separation in the course of time. The micromeulsions are classified into an oil-in-water and a water-in-oil forms, wherein the former is preferable in the present invention. The oil-in-water microemulsion means ultrafine elementary particles protected in the water phase, which is formed by dissolving the drug in the oil phase and then enclosing the drug in the surfactant and/or co-surfactant when the drug is hydrophobic. They have physico-chemical properties that they are thermodynamically stable, allow to disperse the immiscible two liquid phases into a single phase can be prepared spontaneously without putting external energy into the procedures for their preparation, and are apparently transparent since the incident light is totally reflected on the surface of particles due to the low concentration and small size of the enclosed particles as finally prepared, and the like.

The thermodynamic stability of microemulsions can be ensured by selecting a suitable surfactant to reduce the surface tension and further by adding the co-surfactant to increase the fluidity of particle membrane.

In the present invention, poloxamers used as the surfactant have a high hydrophilic/lipophilic balance and therefore, can allow that the composition can be readily prepared in the form of an oil-in-water microemulsion.

First of all, the microemulsion thus prepared can overcome the problem of emulsions due to a instability of the formulation'since it has characteristic features that it is thermodynamically stable in comparison to the known emulsions, can be readily prepared spontaneously at room temperature and is a transparent solution. In addition, it has advantages in that it forms small and uniform particles in size of 100 nm and below so that it can be readily filtered through the filter in size of 0.22 $\mu$m to make a sterile filtration possible and to reduce the risk of embolism to be caused by some large particles and lipid. Further, the hydrophilicity of the stably enclosed drug can sufficiently contribute for reducing the pain when it is injected, since when it is injected via intravenous route, it is dispersed by rapid blood flow to reduce the direct contact with the membrane of blood vessel. Moreover, since it does not contain any lipid component which is used in lipid emulsions, it also reduce the risk of hyperlipidemia which may be raised due to lipid components.

The composition of the present invention can be prepared by further adding an agent for pH adjustment. Although any agent for pH adjustment conventionally used in this may can be used without any special limitation, sodium hydroxide (NaOH) is particularly preferably used. In addition, the composition of the present invention can also contain an agent for isotonicity, if appropriate. Similarly, although any agent for isotonicity conventionally used in this art can be irrespectively used, it is preferable to select glycerol.

The composition of the present invention is typically a sterile, aqueous preparation and has a very small particle size (100 nm and below). Therefore, it can be formulated into an injectable solution in a sterile state by a simple filtration, rather than the final sterilization using autoclave. It is preferred to practice all the procedures for preparation under nitrogen.

The present invention is more specifically explained by the following examples. However, it should, be understood that the scope of the present invention is not limited by the examples in any manner. It will be appreciated by any person skilled in this art that the present invention includes the following examples and further can be variously modified and altered within the technical concept of the present invention.

EXAMPLE 1

As the surfactant, 0.5 g of 407 POLOXAMER 407 (Polyoxyethylene-polyoxypropylene copolymer), 4 g of POLOXAMER 188 (Polyoxyethylene-polyoxypropylene copolymer) and 1 g of SOLUTOL HS 15 (Macrogol-15 Hydroxystearate) were added and dissolved in about 80 g of purified water for injection at room temperature. While stirring, 1 g of propofol was added dropwise to the resulting solution and the stirring was continued until the single phase is formed. 2.08 g of glycerol as an agent for isotonicity was then added thereto. Purified water for injection was added to make 100 ml of the final volume and then, the appropriate amount of sodium hydroxide was added to adjust the pH value to 7.4. The resulting microemulsion was filtered through 0.22 $\mu$M filter to remove the particulate materials and microorganisms. The product thus obtained was introduced into a suitable container which was filled with nitrogen and then, sealed.

EXAMPLE 2

As the surfactant, 0.5 g of POLOXAMER 407 (Polyoxyethylene-polyoxypropylene copolymer) and 5 g of SOLUTOL HS 15 (Macrogol-15 Hydroxystearate) were added and dissolved in about 80 g of purified water for injection at room temperature. While stirring, 1 g of propofol was added dropwise to the resulting solution and the stirring was continued until the single phase is formed. 2.14 g of glycerol as an agent for isotonicity was then added thereto. Purified water for injection was, was added to make 100 ml of the final volume and then, the appropriate amount of sodium hydroxide was added to adjust the pH value to 7.4. The resulting microemulsion was filtered through 0.22 $\mu$m filter to remove the particulate materials and microorganisms. The product thus obtained was introduced into a suitable container which was filled with nitrogen and then, sealed.

EXAMPLE 3

As the surfactant, 0.5 g of POLOXAMER 407 (Polyoxyethylene-polyoxypropylene copolymer), 6 g of POLOXAMER 188 (Polyoxyethylene-polyoxypropylene copolymer) and 0.5 g of egg lecithin were added and dissolved in about 80 g of purified water for injection at room temperature. While stirring, 1 g of propofol was added dropwise to the resulting solution and the stirring was continued until the single phase is formed. 2.0 g of glycerol as an agent for isotonicity was then added thereto. Purified water for injection was added to make 100 ml of the final volume and then, the appropriate amount of sodium hydroxide was added to adjust the pH value to 7.4. The resulting microemulsion was filtered through 0.22 $\mu$m filter to remove the particulate materials and microorganisms. The product thus obtained was introduced into a suitable container which was filled with nitrogen and then, sealed.

EXAMPLE 4

As the surfactant, 0.5 g of POLOXAMER 407 (Polyoxyethylene-polyoxypropylene copolymer), 6 g of SOLUTOL HS 15 (Macrogol-15 Hydroxystearate) and 0.5 g of egg lecithin were added and dissolved in about 80 g of purified water for injection at room temperature. While stirring, 1 g of propofol was added dropwise to the resulting solution and the stirring was continued until the single phase is formed. 2.09 g of glycerol as an agent for isotonicity was then added thereto. Purified water for injection was added to make 100 ml of the final volume and then, the appropriate amount of sodium hydroxide was added to adjust the pH value to 7.4. The resulting microemulsion was filtered through 0.22 $\mu$M filter to remove the particulate materials and microorganisms. The product thus obtained was introduced into a suitable container which was filled with nitrogen and then, sealed.

EXAMPLE 5

As the surfactant, 7 g of POLOXAMER 188 (Polyoxyethylene-polyoxypropylene copolymer) and 1 g of SOLUTOL HS 15 (Macrogol-15 Hydroxystearate) were added and dissolved in about 80 g of purified water for injection at room temperature. While stirring, 1 g of propofol was added dropwise to the resulting solution and the stirring was continued until to the single phase is formed. 2.07 g of glycerol as an agent for isotonicity was then added thereto. Purified water for injection was added to make 100 ml of the final volume and then, the appropriate amount of sodium hydroxide was added to adjust the pH value to 7.4. The resulting microemulsion was filtered through 0.22 μM filter to remove the particulate materials and microorganisms. The product thus obtained was introduced into a suitable container which was filled with nitrogen and then, sealed.

EXAMPLE 6

As the surfactant, 4 g of POLOXAMER 407 (Polyoxyethylene-polyoxypropylene copolymer) was added and dissolved in about 80 g of purified water for injection at room temperature. While stirring, 1 g of propofol was added dropwise to the resulting solution and the stirring was continued until the single phase is formed. As the co-surfactant, 1.5 g of ethanol and 0.5 g of polyethylene glycol 400 were added thereto. Purified water for injection was added to make 100 ml of the final volume. The resulting microemulsion was filtered through 0.22 μM filter to remove the particulate materials and microorganisms. The product thus obtained was introduced into a suitable container which was filled with nitrogen and then, sealed.

EXAMPLE 7

As the surfactant, 8 g of POLOXAMER 188 (Polyoxyethylene-polyoxypropylene copolymer) was added and dissolved in about 80 g of purified water for injection at room temperature. While stirring, 1 g of propofol was added dropwise to the resulting solution and the stirring was continued until the single phase is formed. As the co-surfactant, 5 g of ethanol and 5 g of polyethylene glycol 400 were added thereto. Purified water for injection was added to make 100 ml of the final volume. The resulting microemulsion was filtered through 0.22 μM filter to remove the particulate materials and microorganisms. The product thus obtained was introduced into a suitable container which was filled with nitrogen and then, sealed.

EXAMPLE 8

3.5 g of POLOXAMER 407 (Polyoxyethylene-polyoxypropylene copolymer) as the surfactant and 2 g of TWEEN 80 (polyoxyethylene sorbitan fatty acid esters) as the co-surfactant were added and dissolved in about 80 g of purified water for injection at room temperature. While stirring, 1 g of propofol was added dropwise to the resulting solution and the stirring was continued until the single phase is formed. As the co-surfactant, 1 g of ethanol and 1 g of polyethylene glycol 400 were added thereto. Purified water for injection was added to make 100 ml of the final volume. The resulting microemulsion was filtered through 0.22 μm filter to remove the particulate materials and microorganisms. The product thus obtained was introduced into a suitable container which was filled with nitrogen and then, sealed.

EXAMPLE 9

3.5 g of POLOXAMER 407 (Polyoxyethylene-polyoxypropylene copolymer) as the surfactant and 2 g of lecithin were added and dissolved in about 80 g of purified water for injection at room temperature. While stirring, 1 g of propofol was added dropwise to the resulting solution and the stirring was continued until the single phase is formed. As the co-surfactant, 1 g of ethanol and 1 g of polyethylene glycol 400 were added thereto. Purified water for injection was added to make 1 ml of the final volume. The resulting microemulsion was filtered through 0.22 μm filter to remove the particulate materials and microorganisms. The product thus obtained was introduced into a suitable container which was filled with nitrogen and then, sealed.

EXAMPLE 10

As the surfactant, 2 g of 407 POLOXAMER 407 (Polyoxyethylene-polyoxypropylene copolymer) and 3 g of POLOXAMER 188 (Polyoxyethylene-polyoxypropylene copolymer) were added and dissolved in about 80 g of purified water for injection at room temperature. While stirring, 1 g of propofol was added dropwise to the resulting solution and the stirring was continued until the single phase is formed. As an agent for isotonicity, 2.17 g of glycerol was then added thereto. Purified water for injection was added to make 1 ml of the final volume and then, the appropriate amount of sodium hydroxide was added to adjust the pH value to 7.4. The resulting microemulsion was filtered through 0.22 μm filter to remove the particulate materials and microorganisms. The product thus obtained was introduced into a suitable container which was filled with nitrogen and then, sealed.

EXAMPLE 11

As the surfactant, 5 g of POLOXAMER 407 (Polyoxyethylene-polyoxypropylene copolymer) was added and dissolved in about 80 g of purified water for injection at room temperature. While stirring, 1 g of propofol was added dropwise to the resulting solution and the stirring was continued until the single phase is formed. As an agent for isotonicity, 2.3 g of glycerol was then added thereto. Purified water for injection was added to make 100 ml of the final volume and then, the appropriate amount of sodium hydroxide was added to adjust the pH value to 7.4. The resulting microemulsion was filtered through 0.22 μm filter to remove the particulate materials and microorganisms. The product thus obtained was introduced into a suitable container which was filled with nitrogen and then, sealed.

EXPERIMENT 1

Effect of Poloxamer 407 on Anesthetic Effect and Toxicity

In order to determine the effect of the interaction of POLOXAMER 407 (Polyoxyethylene-polyoxypropylene copolymer) as the surfactant and propofol on the anesthetic effect and toxicity via intravenous injection, the test samples were prepared by combining each of 3%, 4%, 6%, 8% and 10% POLOXAMER 407 (Polyoxyethylene-polyoxypropylene copolymer) with 1% propofol, 1.5% ethanol and 0.5% polyethylene glycol 400 to compare the anesthetic effect and toxicity with each other. As the experimental animal, 5 male Sprague-Dawley rats (160±10 g) were used in each test group and propofol was administered in an amount of 10 mg/kg. The control group received Diprivan which has been currently used in the clinical field. In all the groups, the time from the point immediately after the administration to the point at which the righting response disappears and the animal is recovered was maintained at the mean level of approximately 11±1 minutes. In the animals of all groups, the clinical symptoms and the weight were daily observed during one week after recovery from anesthesia and as the result, it was identified that they were uniform and normal.

According to the test result, it could be found that POLOXAMER 407 (Polyoxyethylene-polyoxypropylene copolymer) has no effect on the anesthetic effect of propofol and further, does not show any symptom of toxicity.

EXPERIMENT 2

Anesthetic Effect

In order to determine the anesthetic effect of the composition of the present invention, the test group received only the formulation of Example 6 and the control group received Diprivan. Rats were placed in the fixed cage. Each formulation was injected into tail vein within 5 to 15 seconds. Rats were then removed from the fixed cage and laid flat. Each of time to unconsciousness, time to startle response, time to righting response and time to full recovery was recorded from the test animals and compared from each other.

significant (p>0.37) according to Standarrd T-test and therefore, the anesthetic effect of the formulation of Example 6 is similar to that of Diprivan of the control group. However, it could be found that the time from righting response to full recovery in the test <Example 6> group is somewhat faster than that of the control group (In the 10 mg/kg test group, the time from righting response to full recovery has a significance level (p) of 0.05 from the Diprivan group).

EXPERIMENT 3

Anesthetic Effect

In order to determine the anesthetic effect of the composition of the present invention in rabbits, the test group received only the formulation of Example 6 and the control group received Diprivan. Rabbits were placed in the fixed cage. Each formulation was injected into tail vein within 30

TABLE 1

Comparison of anesthetic effects in rats

| Drug | Dosage (mg/kg) | Time to unconsciousness (min.) | Time to startle response (min.) | Time to righting response, (min.) | Time to full recovery (min.) |
|---|---|---|---|---|---|
| Example 6 | 5 | <1 | 0.6 ± 0.6 | 3.6 ± 3.5 | 6.4 ± 2.8 |
|  | 10 | <1 | 7.7 ± 1.5 | 9.5 ± 1.7 | 12.7 ± 1.4 |
|  | 15 | <1 | 9.4 ± 2.0 | 12.5 ± 1.3 | 17.2 ± 1.9 |
|  | 20 | <1 | 12.9 ± 2.9 | 16.5 ± 1.8 | 20.5 ± 1.8 |
|  | 25 | <1 | 19.5 ± 2.9 | 25.0 ± 3.2 | 31.8 ± 1.8 |
| Diprivan | 5 | <1 | 0.6 ± 0.3 | 3.9 ± 2.4 | 6.8 ± 1.7 |
|  | 10 | <1 | 6.6 ± 2.1 | 10.5 ± 1.0 | 15.4 ± 1.2 |
|  | 15 | <1 | 9.8 ± 2.9 | 13.3 ± 2.1 | 18.3 ± 3.3 |
|  | 20 | <1 | 13.0 ± 2.5 | 18.3 ± 3.6 | 23.3 ± 3.2 |
|  | 25 | <1 | 21.0 ± 4.5 | 32.5 ± 3.0 | 36.2 ± 2.4 |

Note)
All the values in the table is recorded as the mean ± standard deviation obtained from 5 rats.

According to the experimental result, it could be found that the time to unconsciousness is within 1 minute in all of the groups, and the test<Example 6> group and the control Diprivan group are substantially similar to each other. In addition, it was identified to wake up out of anesthesia is seconds. Rabbits were then removed from the fixed cage and laid flat. Each of time to unconsciousness, time to startle response, time to righting response and time to full recovery was recorded from the test animals and compared from each other.

TABLE 2

Comparison of anesthetic effects in rabbits

| Drug | Dosage (mg/kg) | Time to unconsciousness (sec.) | Time to startle response (min.) | Time to righting response (min.) | Time to full recovery (min.) |
|---|---|---|---|---|---|
| Example 6 | 10 | <5 | 5.2 ± 2.8 | 8.1 ± 1.5 | 12.3 ± 1.8 |
| Diprivan | 10 | <5 | 5.1 ± 0.9 | 9.1 ± 1.9 | 13.4 ± 2.1 |

Note)
All the values in the table is recorded as the mean ± SD obtained from 5 rabbits.

As can be seen from Table 2, it could be found that the anesthetic effect of the test <Example 6> Group is Substantially Similar to That of the Control Diprivan group.

EXPERIMENT 4

Anesthetic Effect in Laparotomy

The test was practiced to determine the anesthetic effect of the formulation of Example 6 in laparotomy 8 weeks-old rats were anesthetized with ether and then the hair he test was cut from the abdominal portion. After rabbits were recovered from ether anesthesia, the formulation was administered through the catheter inserted into tail vein. After 5 minutes from anesthesia induction, the abdominal portion was incised to about 3 cm and the formulation was repeatedly injected to maintain the anesthetic state for about 60 minutes. At the time of 45 minutes of anesthetic maintenance, the incised portion was ligated and then, each of time to unconsciousness, time to startle response, time to righting response and time to full recovery was recorded.

TABLE 3

Anesthetic effect in laparotomy

| No. | Time to unconsciousness (min.) | Total Dosage (mg/kg) | Time to startle response (min.) | Time to righting response (min.) | Time to full recovery (min.) |
|---|---|---|---|---|---|
| 1 | <1 | 40.0 | 64.0 | 68.0 | 74.5 |
| 2 | <1 | 40.0 | 56.0 | 68.0 | 72.0 |
| 3 | <1 | 41.3 | 57.5 | 58.9 | 67.9 |
| 4 | <1 | 40.0 | 64.0 | 67.8 | 71.3 |
| 5 | <1 | 37.5 | 55.0 | 62.4 | 72.0 |
| Mean | | 39.8 | 59.3 | 65.0 | 71.5 |
| S.D. | | 1.38 | 4.38 | 4.18 | 2.37 |

During anesthesia induction, the total dosage of the formulation required to maintain the anesthetic state was about 38.9 mg/kg, and the time to full recovery was recorded as 71.5 minutes. After laparotomy, any abnormal change was not observed in rabbits.

EXPERIMENT 5

Induction of Anesthetia and Toxicity

To determine $HD_{50}$ which is the amount administered for induction of anesthesia, and $LD_{50}$ which is the amount at which the lethal rate reaches 50% after drug administration, in the test <Example 6> group and the control Diprivan group, each test drug was injected into tail vein of each of 10 male mice with gradually increasing the amount. As the result of experiment, $HD_{50}$ and $LD_{50}$ values of the formulation of Example 6 were found to be 115 mg/kg and 56.0 mg/kg, respectively, whereas in the control Diprivan group $HD_{50}$ and $LD_{50}$ were found to be 10.5 mg/kg and 53.0 mg/kg, respectively. Thus, it could be identified that the formulation of Example 6 exhibits the similar result to Diprivan.

EXPERIMENT 6

Side effects

The formulation of Example 6 was injected into ear vein of each of three rabbits in a total amount of 3 ml at the rate of 1 ml/min. After 30 minutes, and 1, 1.5, 2, 4, 6 and 24 hours, each injection site was macroscopically observed for the responses caused by pain and phlebitis. As the result, the resistant behaviour caused by pain from injection, and any change of phlebitis such as rubor, erythema, edema, etc. could not be observed.

EXPERIMENT 7

Hemolysis

To determine the hemolysis of the formulation of Example 6, albino rat was incised with scissor at the upper part of left femoral region, at which each of vein and artery was cannulated, and then 10 mg/kg of the formulated drug was intravenously injected over one minute. After 0, 5, 10, 15, 30, 45 and 60 minutes, blood was collected from femoral artery in an amount of 100 μl each time. Blood was obtained after heparin-physiological saline and some blood filled in the catheter were removed few, seconds before collecting blood each time. After blood was collected, a small amount of heparin-physiological saline was introduced into the catheter connecting tube to prevent blood coagulation. 100 μl of the collected blood were mixed with 500 μl of physiological saline and then centrifuged with 3000 rpm for 10 minutes. 100 μl of the supernatant were transferred into microplate and the absorbance of released hemoglobin was measured at 540 nm. Hemolysis (%) was calculated according to the following equation. The control group used 70% propylene glycol (PG) solution.

$$\text{Hemolysis \%} = (A_f - A_0)/(A_{100} - A_0) \times 100$$

In the above equation, $A_{100}$ is the absorbance at the time of 100% hemolysis (100 μl of blood was mixed with 500 μl of water); $A_0$ is the absorbance at the time of 0% hemolysis as the blank (Before injection of the drug, normal blood was mixed with 500 μl of physiological saline for the blank test), and $A_f$ is the absorbance of each specimen.

TABLE 4

Hemolysis of the formulation of Example 6

| | | | $A_f$ | | | | | |
|---|---|---|---|---|---|---|---|---|
| $A_{100}$ | $A_0$ | initial | 5 min. | 10 min. | 15 min. | 30 min. | 45 min. | 60 min. |
| 4.088 | 0.005 | 0.003 | 0.005 | 0.005 | 0.000 | 0.002 | 0.000 | 0.004 |
| Hemolysis (%) | | 0 | 0 | 0 | 0 | 0 | 0 | 0 |

TABLE 5

Hemolysis of 70% PG

| | | | $A_f$ | | | | | |
|---|---|---|---|---|---|---|---|---|
| $A_{100}$ | $A_0$ | initial | 5 min. | 10 min. | 15 min. | 30 min. | 45 min. | 60 min. |
| 4.076 | 0.007 | 0.081 | 0.086 | 0.091 | 0.067 | 0.038 | 0.047 | 0.041 |
| Hemolysis (%) | | 1.82 | 1.94 | 2.06 | 1.47 | 0.76 | 0.98 | 0.84 |

It could be found that the formulation of Example 6 shows the similar absorbance to the blank test and thus, does substantially not cause hemolysis whereas 70% PG as the control group shows the absorbance 80–90 times as high as the formulation of Example 6 and causes hemolysis.

EXPERIMENT 8

Effect of the Continuous Intravenous Injection for 12 Hours on Pharmacological and Blood Biochemical Change Using Beagle dog About 9 months-old male beagle dogs weighing about 8.7–12.4 kg were purchased and then used in the experiment after acclimation for 22–23 days. Each of the test material (Example 1) and the positive comparative material (Diprivan) was administered into cephalic vein at the rate of 60 mg/kg/hr. Observation and examination were practiced for all test animals as follows.

1) Observation of General Symptoms and Death

During the period for maintaining the administration of the relevant drug, the symptoms including intoxication, dyspnea, abnormal behaviour, appearance and death were continuously observed.

2) Determination of Blood Pressure and Heart Rate

The blood pressure and heart rate were measured by connecting the catheter with the measuring equipment (data acquisition system, Biopak, USA). After the stabilization of blood pressure for about 20 minutes was identified, the test material (Example 1) and the positive comparative material (Diprivan) were administered for 12 hours. During the total period of the experiment, the test animal was maintained under continuous ventilation by inserting the tracheal tube into the test animal and controlling the stroke volume as 200–250 and spm as 20–30 by means of a ventilator. The blood pressure and heart rate were measured for 12 hours and represented by the change percent (%) relative to the values measured before drug administration.

3) Blood Biochemical Examination

To analyse glucose, total cholesterol and triglyceride values for blood biochemical examination, blood was collected before administration of the drug and every hour for 12 hours after administration. The collected blood was placed in the serum separating tube and then centrifuged with 300 rpm for 10 minutes. The separated serum was transferred into the Eppendorf tube and stored in a deep freezer for use in the subsequent experiment.

4) Blood gas Examination

Blood was collected from right femoral artery before administration of the drug and at interval of one hour for 12 hours after administration and then, measured $O_2$ and $CO_2$ partial pressure and pH of arterial blood using a blood gas analyzer.

As the result of Experiment 8, in both the group receiving the test material (Example 1) and the group receiving the positive comparative material (Diprivan) no dead animal was found. As the general symptoms, during the period of maintaining anesthesia, the group receiving the positive comparative material (Diprivan) was observed to show vomiting, some tremor and dyspnea whereas the group receiving the test material (Example 1) did not show any particular symptom. In observing the blood pressure and heart pressure, the blood pressure was somewhat lowered after administration of the test material (Example 1) and the positive comparative material (Diprivan) and observed as showing a tendency to somewhat return to the level before drug administration in the group receiving the positive comparative material (Diprivan). Although the group receiving the test material (Example 1) showed somewhat change in the blood pressure, such change was not significantly different from that of the group receiving the positive comparative material (Diprivan). Meanwhile, the heart rate was more greatly increased in the group receiving the test material (Example 1) in comparison to the group receiving the positive comparative material (Diprivan), in the course of time.

In the blood biochemical examination, the glucose level was not greatly varied both in the group receiving the test formulation (Example 1) and the group receiving the positive comparative formulation (Diprivan) and did not show a tendency to increase and decrease in the course of time. The total cholesterol level exhibited a tendency to somewhat increase in comparison to that before drug administration both in the group receiving the test formulation (Example 1) and the group receiving the positive comparative formulation (Diprivan), in the course of time, and is slightly higher generally in the group receiving the positive comparative formulation (Diprivan) than that in the group receiving the test formulation (Example 1). In addition, it could be found that triglyceride level in the group receiving the positive comparative formulation (Diprivan) exhibits a high tendency to increase about 30–50 times in course of time in comparison to that immediately before drug administration whereas in the group receiving the test formulation (Example 1) it exhibits a tendency to increase about 3–5 times in course of time in comparison to that immediately before drug administration. Further, in the course of time the triglyceride level in the group receiving the positive comparative formulation (Diprivan) is generally higher about 3–5 times than that in the group receiving the test formulation (Example 1).

As the result of the blood gas examination, both the group receiving the test formulation (Example 1) and the group receiving the positive comparative formulation (Diprivan) maintained the constant pH level. The $CO_2$ partial pressure exhibited a tendency to slightly increase in the course of time in the group receiving the positive comparative formulation (Diprivan) but maintained at the constant level in the group receiving the test formulation (Example 1). In addition, the $O_2$ partial pressure was somewhat lowered in the course of time both in the group receiving the test formulation (Example 1) and the group receiving the positive comparative formulation (Diprivan) but was generally somewhat higher in the group receiving the test formulation (Example 1).

TABLE 6

Change in blood biochemical data of beagle dogs receiving the formulation of Example 1 and the comparative drug Diprivan

| | Diprivan | | | Example 1 | | |
|---|---|---|---|---|---|---|
| Hours | glucose | T-CHO | TG | glucose | T-CHO | TG |
| 0 | 94.9 ± 36.0 | 183.1 ± 24.1 | 36.6 ± 3.6 | 113.7 ± 19.7 | 156.0 ± 26.4 | 22.0 ± 3.9 |
| 1 | 125.4 ± 7.1 | 194.1 ± 7.8 | 365.0 ± 133.3 | 119.4 ± 10.5 | 148.6 ± 28.7 | 32.6 ± 18.0 |
| 2 | 133.1 ± 11.3 | 211.6 ± 9.1 | 552.1 ± 199.7 | 120.8 ± 19.2 | 154.6 ± 26.8 | 56.0 ± 40.6 |
| 3 | 131.2 ± 5.4 | 221.9 ± 9.3 | 706.3 ± 284.1 | 125.2 ± 10.6 | 158.4 ± 26.9 | 91.1 ± 43.2 |
| 4 | 138.4 ± 8.5 | 240.1 ± 6.3 | 891.4 ± 398.6 | 115.6 ± 14.8 | 168.7 ± 30.4 | 130.5 ± 48.6 |
| 5 | 76.2 ± 83.5 | 137.4 ± 137.5 | 684.5 ± 437.8 | 120.9 ± 18.4 | 166.8 ± 24.0 | 169.8 ± 67.9 |
| 6 | 119.7 ± 67.9 | 209.3 ± 117.3 | 1130.2 ± 780.8 | 121.7 ± 19.8 | 184.8 ± 34.9 | 180.8 ± 86.0 |

TABLE 6-continued

Change in blood biochemical data of beagle dogs receiving the formulation of Example 1 and the comparative drug Diprivan

| | Diprivan | | | Example 1 | | |
|---|---|---|---|---|---|---|
| Hours | glucose | T-CHO | TG | glucose | T-CHO | TG |
| 7 | 161.9 ± 51.7 | 288.5 ± 27.1 | 1251.1 ± 478.9 | 119.2 ± 22.2 | 177.3 ± 26.8 | 207.8 ± 45.7 |
| 8 | 155.3 ± 24.7 | 307.0 ± 21.5 | 1421.1 ± 468.1 | 94.5 ± 54.2 | 147.1 ± 68.8 | 232.2 ± 70.4 |
| 9 | 124.0 ± 52.4 | 270.6 ± 101.0 | 1430.7 ± 350.7 | 125.1 ± 19.4 | 185.0 ± 23.0 | 242.5 ± 48.6 |
| 10 | 105.0 ± 69.8 | 250.8 ± 162.1 | 1408.2 ± 462.9 | 111.5 ± 9.9 | 188.8 ± 17.3 | 268.2 ± 51.5 |
| 11 | 137.6 ± 13.4 | 370.8 ± 25.8 | 1549.2 ± 488.0 | 120.7 ± 10.6 | 189.3 ± 21.7 | 275.0 ± 38.5 |
| 12 | 91.8 ± 85.6 | 214.7 ± 175.5 | 1367.2 ± 346.0 | 95.8 ± 65.2 | 185.4 ± 17.3 | 236.1 ± 123.7 |

TABLE 7

Arterial blood pressure in beagle dogs receiving the formulation of Example 1 and the comparative drug Diprivan (n = 4)

| | Diprivan | | Example 1 | |
|---|---|---|---|---|
| Hours | Mean (%) | S.E.M. | Mean (%) | S.E.M. |
| 0 | 0.00 | 0.00 | 0.00 | 0.00 |
| 1 | −9.55 | 7.81 | −18.01 | 1.85 |
| 2 | −7.24 | 7.24 | −7.53 | 7.01 |
| 3 | −2.89 | 6.95 | −4.10 | 5.28 |
| 4 | −5.34 | 6.16 | −4.87 | 5.52 |
| 5 | −1.37 | 5.90 | −1.75 | 2.19 |
| 6 | −6.24 | 7.46 | −1.22 | 2.28 |
| 7 | −2.19 | 7.86 | −0.51 | 3.34 |
| 8 | −8.86 | 5.74 | −0.07 | 3.23 |
| 9 | −4.99 | 9.92 | −0.93 | 3.13 |
| 10 | −6.67 | 9.43 | −4.30 | 0.98 |
| 11 | −0.14 | 12.51 | −7.79 | 0.89 |
| 12 | −0.72 | 9.91 | −3.19 | 4.48 |
| Initial value (mmHg) | 169.8 | 10.57 | 159.7 | 12.85 |

TABLE 8

Heart rate in beagle dogs receiving the formulation of Example 1 and the comparative drug Diprivan (n = 4)

| | Diprivan | | Example 1 | |
|---|---|---|---|---|
| Hours | Mean (%) | S.E.M. | Mean (%) | S.E.M. |
| 0 | 0.00 | 0.00 | 0.00 | 0.00 |
| 1 | −0.82 | 20.52 | 12.39 | 14.62 |
| 2 | 1.04 | 24.37 | 18.63 | 12.92 |
| 3 | −1.64 | 27.50 | 14.61 | 12.83 |
| 4 | 0.23 | 26.48 | 12.20 | 16.56 |
| 5 | 3.78 | 28.44 | 2.70 | 15.89 |
| 6 | 0.36 | 20.40 | 12.94 | 19.68 |
| 7 | 1.72 | 20.57 | 21.81 | 25.48 |
| 8 | 10.72 | 12.10 | 17.80 | 22.25 |
| 9 | 15.47 | 13.63 | 23.83 | 21.67 |
| 10 | 20.47 | 14.61 | 20.48 | 21.82 |
| 11 | 12.90 | 14.70 | 20.66 | 19.26 |
| 12 | 12.65 | 15.99 | 29.43 | 24.16 |
| Initial value (heart rate/min.) | 113.9 | 14.21 | 103.3 | 12.31 |

TABLE 9

Blood gas level in beagle dogs receiving the formulation of Example 1 and the comparative drug Diprivan (n = 4)

| | Diprivan | | | Example 1 | | |
|---|---|---|---|---|---|---|
| Hours | pH | $PCO_2$ | $PO_2$ | pH | $PCO_2$ | $PO_2$ |
| 0 | 7.33 ± 0.04 | 43.3 ± 14.5 | 85.8 ± 5.1 | 7.40 ± 0.15 | 37.1 ± 6.0 | 91.7 ± 2.9 |
| 1 | 7.26 ± 0.05 | 43.1 ± 5.6 | 86.8 ± 11.1 | 7.29 ± 0.03 | 48.1 ± 6.9 | 87.1 ± 9.8 |
| 2 | 7.34 ± 0.18 | 40.4 ± 10.7 | 81.3 ± 6.4 | 7.28 ± 0.04 | 48.2 ± 4.9 | 85.0 ± 14.2 |
| 3 | 7.28 ± 0.04 | 46.6 ± 3.2 | 76.6 ± 9.6 | 7.26 ± 0.04 | 48.3 ± 4.7 | 84.1 ± 9.5 |
| 4 | 7.27 ± 0.02 | 48.6 ± 6.3 | 72.0 ± 5.8 | 7.29 ± 0.07 | 49.2 ± 5.3 | 76.3 ± 10.9 |
| 5 | 7.24 ± 0.03 | 47.5 ± 5.8 | 77.4 ± 19.0 | 7.29 ± 0.04 | 45.3 ± 6.2 | 82.9 ± 10.9 |
| 6 | 7.27 ± 0.05 | 45.3 ± 4.0 | 74.6 ± 9.3 | 7.28 ± 0.04 | 46.9 ± 5.6 | 84.4 ± 11.6 |
| 7 | 7.32 ± 0.09 | 42.5 ± 1.8 | 74.1 ± 6.4 | 7.30 ± 0.04 | 44.8 ± 5.0 | 88.1 ± 13.8 |
| 8 | 7.26 ± 0.04 | 48.2 ± 4.8 | 74.2 ± 5.8 | 7.30 ± 0.06 | 45.4 ± 7.3 | 79.3 ± 11.1 |
| 9 | 7.31 ± 0.12 | 47.2 ± 7.9 | 64.8 ± 11.0 | 7.30 ± 0.04 | 45.2 ± 4.3 | 80.7 ± 8.3 |
| 10 | 7.26 ± 0.08 | 52.1 ± 6.9 | 60.1 ± 12.3 | 7.31 ± 0.04 | 47.3 ± 5.1 | 74.8 ± 4.8 |
| 11 | 7.25 ± 0.12 | 57.3 ± 12.3 | 47.2 ± 15.8 | 7.27 ± 0.05 | 50.7 ± 5.2 | 71.0 ± 14.0 |
| 12 | 7.22 ± 0.07 | 61.1 ± 13.6 | 53.5 ± 20.0 | 7.28 ± 0.07 | 42.9 ± 18.8 | 73.0 ± 8.2 |

The present invention provides an anesthetic composition for intravenous injection, which is prepared in the form of a microemulsion by adding a POLOXAMER and optionally, at least one selected from the group consisting of SOLUTOL HS 15 (Macrogol-15 Hydroxystearate), egg lecithin, LABRASOL (Polyoxy capryllic glyceride), polyoxy 10 oleyl ether, TWEEN (polyoxyethylene sorbitan fatty acid esters), ethanol and polyethylene glycol, to propofol. The composition of the present invention is composed of small particles of 100 nm and below, to thermodynamically stable, and does not cause the phase separation in the course of time. Further, since it can be aseptically filtered to remove the microorganisms contamination, it has advantages that a separate sterilization procedure is unnecessary so that it can be readily prepared at a low cost by a simple procedure. In addition, since the composition of the present invention is hydrophilic and is composed of small particles so that it can be dispersed by rapid blood flow in the case of intravenous injection, it results in a little pain at injection site and substantially does not cause embolism and also does not cause hemolysis.

What is claimed is:

1. An anesthetic composition for intravenous injection, comprising propofol and POLOXAMER 407 (Polyoxyethylene-polyoxypropylene copolymer) as surfactant, wherein the composition is in the form of an oil-in-water microemulsion having a particle size of 100 nm and below.

2. The composition according to claim 1, wherein the content of said POLOXAMER (Polyoxyethylene-polyoxypropylene copolymer) comprises 0.1 to 10% by weight of the total composition.

3. The composition according to claim 1, wherein propofol is contained in an amount of 1 to 2% by weight of the total composition.

4. The composition according to claim 1, wherein it further comprises at least one co-surfactant selected from the group consisting of SOLUTOL HS 15 (Macrogol-15 Hydroxystearate), egg lecithin, LABRASOL (Polyoxy capryllic glyceride), polyoxy 10 oleyl ether, TWEEN (polyoxyethylene sorbitan fatty acid esters), ethanol and polyethylene glycol.

5. The composition according to claim 1, wherein said POLOXAMER 407 (Polyoxyethylene-polyoxypropylene copolymer) is contained in an amount of 0.1 to 5% by weight of the total composition.

6. The composition according to claim 4, wherein said SOLUTOL HS 15 (Macrogol-15 Hydroxystearate) is contained in an amount of 0.1 to 10% by weight of the total composition.

7. The composition according to claim 4, wherein said egg lecithin is contained in an amount of 0.1 to 5% by weight of the total composition.

* * * * *